(12) United States Patent
Yanaga et al.

(10) Patent No.: US 11,427,808 B2
(45) Date of Patent: Aug. 30, 2022

(54) METHOD FOR SERUM-FREE CULTURE OF CHONDROCYTES AND SERUM-FREE CULTURE MEDIUM

(71) Applicant: Regenesis Science Co., Ltd., Fukuoka (JP)

(72) Inventors: Hiroko Yanaga, Fukuoka (JP); Katsu Yanaga, Fukuoka (JP)

(73) Assignee: Regenesis Science Co., Ltd., Fukuoka (JP)

(*) Notice: Subject to any disclaimer, the term of this patent is extended or adjusted under 35 U.S.C. 154(b) by 0 days.

(21) Appl. No.: 15/310,442

(22) PCT Filed: Oct. 26, 2015

(86) PCT No.: PCT/JP2015/080139
§ 371 (c)(1),
(2) Date: Nov. 10, 2016

(87) PCT Pub. No.: WO2016/076102
PCT Pub. Date: May 19, 2016

(65) Prior Publication Data
US 2017/0306294 A1     Oct. 26, 2017

(30) Foreign Application Priority Data

Nov. 14, 2014   (JP) .............................. JP2014-231489

(51) Int. Cl.
*C12N 5/077*     (2010.01)
*C12N 1/00*      (2006.01)

(52) U.S. Cl.
CPC ............. *C12N 5/0655* (2013.01); *C12N 1/00* (2013.01); *C12N 2500/36* (2013.01); *C12N 2500/38* (2013.01); *C12N 2500/90* (2013.01); *C12N 2501/105* (2013.01); *C12N 2501/115* (2013.01); *C12N 2501/33* (2013.01); *C12N 2501/734* (2013.01); *C12N 2501/999* (2013.01)

(58) Field of Classification Search
None
See application file for complete search history.

(56) References Cited

U.S. PATENT DOCUMENTS

| | | | | |
|---|---|---|---|---|
| 6,150,163 A | * | 11/2000 | McPherson | C12N 5/0655 435/383 |
| 2005/0090002 A1 | * | 4/2005 | Canceda | C12N 5/0655 435/366 |
| 2007/0292949 A1 | * | 12/2007 | Duguay | C12N 5/0655 435/366 |

FOREIGN PATENT DOCUMENTS

| | | |
|---|---|---|
| CN | 104120105 A | 10/2014 |
| EP | WO0027996 A1 | 5/2000 |
| JP | 2000-515023 A | 11/2000 |
| JP | 2002-529071 A | 9/2002 |
| JP | 2003-125787 A | 5/2003 |
| JP | 0003638614 B | 1/2005 |
| JP | 2008-136396 A | 6/2008 |
| JP | 2009-540826 A | 11/2009 |
| JP | WO2014/084085 A1 | 6/2014 |
| JP | 2015-522590 A | 8/2015 |
| WO | WO2007149328 A1 | 12/2007 |

OTHER PUBLICATIONS

Chua et al., Insulin-Transferrin-Selenium Prevent Human Chondrocyte Dedifferentiation and Promote the Formation of High Quality Tissue Engineered Human Hyaline Cartilage, Ke uHro Cpheuana eCt ealll.s and Materials vol. 9. 2 0 0 5 (pp. 58-67).*
Mandi et al., Fibroblast growth factor-2 in serum-free medium is a potent mitogen and reduces dedifferentiation of human ear chondrocytes in monolayer culture, Matrix Biology 23 (2004) 231-241.*
Kato et al., Growth Requirements of Low-Density Rabbit Costal Chondrocyte Cultures Maintained in Serum-Free Medium, Journal of Cellular Physiology 120:354-363 (1984).*
Langle et al., Small Molecules Targeting in Vivo Tissue Regeneration, Stem Cell Biology and Regenerative Medicine, ACS Chem. Biol. 2014, 9, 57-71.*
FGF2, UniProt Entry, Webpage, 2018.*
Yanaga et al., Cell-Engineered Human Elastic Chondrocytes Regenerate Natural Scaffold In Vitro and Neocartilage with Neoperichondrium in the Human Body Post-Transplantation, Tissue Engineering: Part A, vol. 18, Nos. 19 and 20, 2012 (Year: 2012).*
Mandi et al., Fibroblast growth factor-2 in serum-free medium is a potent mitogen and reduces dedifferentiation of human ear chondrocytes in monolayer culture, Matrix Biology 23 (2004) 231-241 (Year: 2004).*
Malicev et al., Comparison of Articular and Auricular Cartilage as a Cell Source for the Autologous Chondrocyte Implantation, J Orthop Res 27:943-948, 2009 (Year: 2009).*
Mandi et al., Serum-Free Medium Supplemented with High-Concentration FGF2 for Cell Expansion Culture of Human Ear Chondrocytes Promotes Redifferentiation Capacity, Tissue Engineering, vol. 8, No. 4, 2002 (Year: 2002).*
ITS, ITS+1 Liquid Media Supplement (100x), Sigma Aldrich, Catalog, 2021 (Year: 2021).*
Ma et al., Gene expression profiling of dedifferentiated human articular chondrocytes in monolayer culture, Osteoarthritis and Cartilage 21 (2013) 599-603 (Year: 2013).*

(Continued)

*Primary Examiner* — Louise W Humphrey
*Assistant Examiner* — Srikanth Patury
(74) *Attorney, Agent, or Firm* — Pyprus Pte Ltd; George D. Liu

(57) ABSTRACT

To provide a method for serum-free culture of human cartilage cells and a serum-free culture medium. A method for serum-free culture of cartilage cells, said method comprising: an enzymatic treatment step for treating a human cartilage cell-containing tissue with a protease; an inhibitor-treatment step for, after the enzymatic treatment step, treating the tissue with an inhibitor for the aforesaid protease; and a culture step for, after the inhibitor-treatment step, culturing the tissue in a serum-free culture medium that contains kartogenin and/or SAG, ITS, FGF2 and hydrocortisone. A serum-free culture medium for culturing cartilage cells, said serum-free culture medium containing kartogenin and/or SAG, ITS, FGF2 and hydrocortisone.

5 Claims, 13 Drawing Sheets

(56) References Cited

OTHER PUBLICATIONS

Duan et al., Epigenetic regulation in chondrocyte phenotype maintenance for cell-based cartilage repair, Am J Transl Res 2015;7(11):2127-2140 (Year: 2015).*

Rohatgi et al., Hedgehog signal transduction by Smoothened: Pharmacologic evidence for a 2-step activation process, PNAS, Mar. 3, 2009, vol. 106, No. 9, pp. 3196-3201 (Year: 2009).*

International Search Report of International Application No. PCT/JP2015/080139 completed Jan. 8, 2016 and dated Jan. 19, 2016 (4 pages).

Long, F. et al., Genetic manipulation of hedgehog signaling in the endochondral skeleton reveals a direct role in the regulation of chondrocyte proliferation, Development, Dec. 15, 2001, 128(24), pp. 5099-5108.

Chen, J. K. et al., Small molecule modulation of Smoothened activity, Proceedings of the National Academy of Sciences of the United States of America, Oct. 21, 2002, 99(22), pp. 14071-14076.

Johnson, K. et al., A stem cell-based approah to cartilage repair, Science, Apr. 5, 2012, 336(6082), pp. 717-721.

First Examination Opinion of Chinese Patent Application No. 201580024032.8 dated Mar. 5, 2019 (6pages).

Hironori Hojo et al., Hedgehog-Gli Activators Direct Osteochondrogenic Function of Bone Morphogenetic Protein Toward OsteoGenesis in the Perichondrium, JJ Bio Chem, 288, 14th, p. 9924-9932, Apr. 5, 2013.

* cited by examiner

Serum-free culture method for cultured cartilage
Primary culture (×100)

day19 day32 day23 day37 day28 day41

Serum-free culture method for cultured cartilage
Primary culture   Control (×100)

day1 day5

METHOD FOR SERUM-FREE CULTURE OF CHONDROCYTES AND SERUM-FREE CULTURE MEDIUM

TECHNICAL FIELD

The present invention relates to a method for culturing chondrocytes, in which cells are treated with a protease before serum-free culture is carried out, and a serum-free culture medium which is suitable for the method.

BACKGROUND ART

JP 2003-125787 A discloses a serum-free culture medium used for differentiation culture of chondrocytes, and a method for culturing chondrocytes using the serum-free culture medium.

JP 3638614 B2 discloses a culture medium for chondrocytes and a method for culturing chondrocytes using the culture medium. The document further discloses ITS.

JP 2002-529071 A discloses a serum-free culture medium for chondrocyte-like cells.

JP 2009-540826 A discloses a method for culturing chondrocytes in which primary human chondrocytes are isolated from a fresh sample of articular cartilage, and subjected to enzymatic digestion using a protease (*Streptomyces griseus*) for an hour, and then subjected to enzymatic digestion with a collagenase. The document discloses to use a collagenase to peel off chondrocytes from cartilage. When a collagenase excessively acts, cells are damaged. Therefore, if serum-free culture is used while a collagenase is attached to cells, chondrocytes cannot be successfully cultured, and further the obtained chondrocytes are not suitable for e.g. a transplant in some cases.

Paragraph [0145] in JP 2015-522590 A discloses that kartogenin is a small molecule which helps to treat osteoarthritis.

CITATION LIST

Patent Document

Patent Document 1: JP 2003-125787 A
Patent Document 2: JP 3638614 B2
Patent Document 3: JP 2002-529071 A
Patent Document 4: JP 2009-540826 A
Patent Document 5: JP 2015-522590 A

SUMMARY OF INVENTION

Technical Problem

In the above-mentioned culture method, cartilage is cultured, but when, for example, the cartilage practically cultured is intended to be transplanted, good results have not been obtained in some cases.

Therefore, an object of the present invention is to provide a method for serum-free culture of chondrocytes, by which culture can be effectively done and good transplant results can be obtained, and a serum-free culture medium which can be used for the method.

Solution to Problem

A first aspect of the present invention relates to a serum-free culture medium for culturing chondrocytes. This culture medium contains one or both of kartogenin and SAG (a smoothened agonist), and ITS, FGF2 and hydrocortisone.

This culture medium preferably contains both kartogenin and SAG.

This culture medium preferably further contains IGF (insulin-like growth factor).

This culture medium preferably further contains chondrocytes, which are to be cultured.

A preferred mode to use this culture medium is preferably a culture medium kit including this culture medium, an ascorbic acid agent and a fatty acid agent, wherein the ascorbic acid agent includes ascorbic acid, an ascorbic acid salt or an ascorbic acid solvate, and the fatty acid agent includes a fatty acid, a fatty acid salt or a fatty acid solvate.

A second aspect of the present invention relates to a method for serum-free culture of chondrocytes. This method is a method for serum-free culture of chondrocytes, including in this order:

an enzymatic treatment step for treating a human chondrocyte-containing tissue with a collagenase, and a culture step for culturing the tissue in a serum-free culture medium, the serum-free culture medium containing one or both of kartogenin and SAG, and ITS, FGF2 and hydrocortisone, wherein the culture step includes:

a step for adding ascorbic acid, an ascorbic acid salt or an ascorbic acid solvate to the serum-free culture medium during a period from the 3rd day to 28th day after the onset of culture, and adding a fatty acid, a fatty acid salt or a fatty acid solvate to the serum-free during a period from the 3rd day to 28th day after the onset of culture.

It is preferred that this method further include an inhibitor-treatment step for treating the tissue with a collagenase inhibitor after the enzymatic treatment step.

Advantageous Effects of Invention

The present invention provides a method for serum-free culture of chondrocytes, by which culture can be effectively done and good transplant results can be obtained, and a serum-free culture medium which can be used for the method.

DESCRIPTION OF EMBODIMENTS

Figure 1:
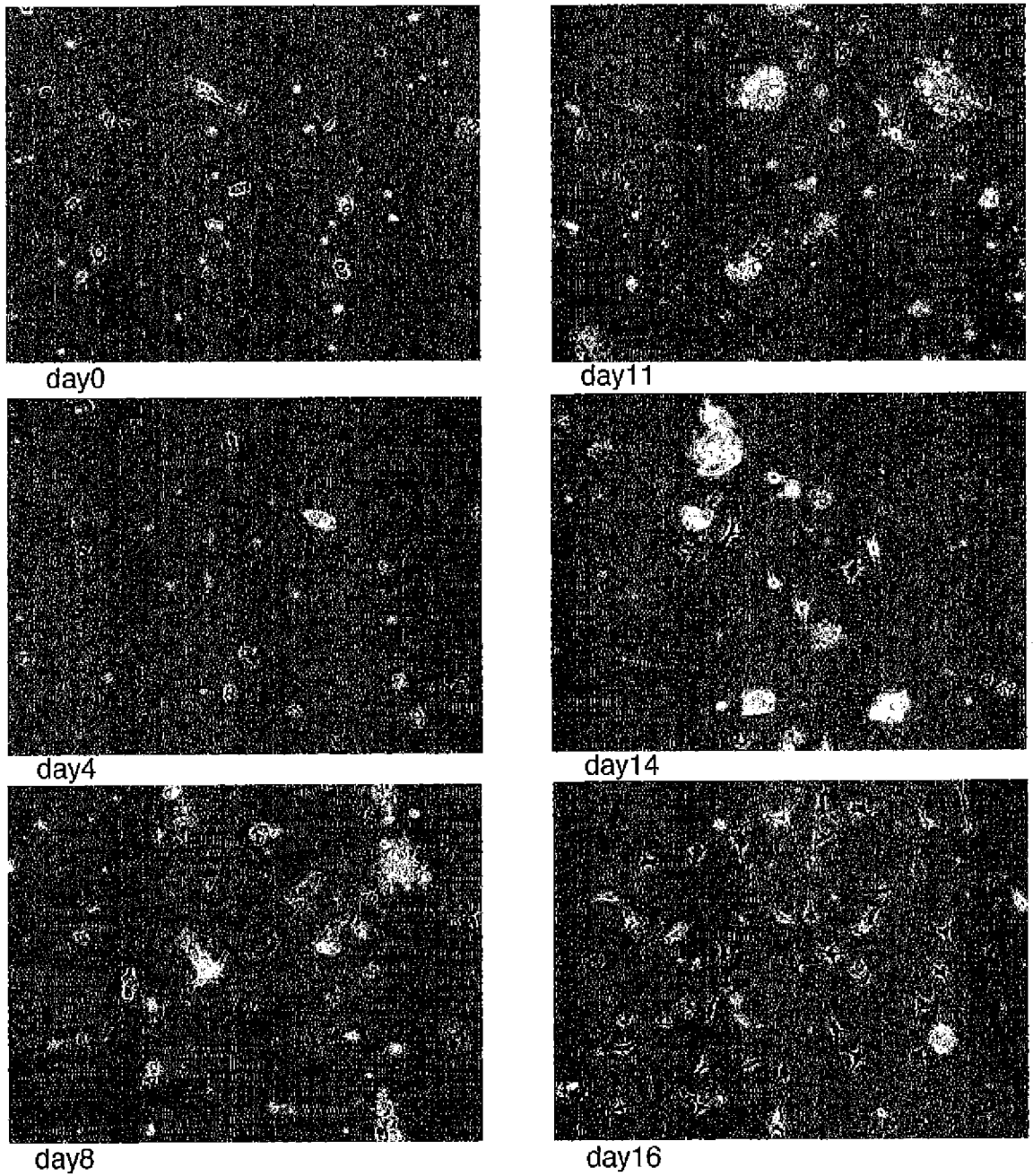
FIG. 1 is a photograph substituted for drawings showing the cultured chondrocytes from the 0th day to 16th day of culture in Example 1.

We explain a mode for carrying out the present invention using drawings. The present invention is not limited to the mode described below, and encompasses modifications appropriately made within the scope obvious to one skilled in the art from the following mode.

The present invention relates to a method for serum-free culture of chondrocytes. This method includes an enzymatic treatment step and a culture step. This method can include an inhibitor-treatment step.

The enzymatic treatment step is a step for treating a human chondrocyte-containing tissue with a protease. To be more specific, the step is a step for bringing a human chondrocyte-containing tissue into contact with a protease to decompose proteins contained in the human chondrocyte-containing tissue with the protease. The treatment with a protease itself has been already known, and thus this step can be carried out based on an already known method.

Examples of human chondrocytes are auricular cartilage, nasal septal cartilage, costal cartilage, articular cartilage, intervertebral cartilage, trachea cartilage, chondrocytes collected from epiglottis, and human chondrocytes cultured from human genes. A method for taking human chondrocytes is known. That is, human chondrocytes can be surgically collected from a patient. In addition, the present invention may obtain human chondrocytes appropriately using cells which can be differentiated into chondrocytes. Cells derived from bone marrow of human and warm-blooded animals, cells derived from articular cartilage, cells derived from skin, embryonic cells, and cells derived from a fetus may be used. Examples of cells which can be differentiated into chondrocytes are human mesenchymal stem cells and dedifferentiated chondrocytes (e.g. dedifferentiated normal human chondrocytes).

In the present invention, a human cartilage tissue and aggregated chondrocytes are treated with a protease to obtain single cells. This step is a digestion step for decomposing a part of proteins contained in the human cartilage tissue and aggregated cells with a protease. Examples of proteases are trypsin or collagenases. Collagenases are known compounds as disclosed in, for example, JP 4764006 B2, JP 5322637 B2, and JP 2009-540826 A. The collagenases are preferably collagenases which do not contain components derived from animals. Such collagenases are on the market, and thus a collagenase which does not contain components derived from animals can be purchased. This solution may appropriately contain known antibiotics such as penicillin and streptomycin. The enzymatic treatment step is, for example, only necessary to prepare a solution containing a protease and to immerse human chondrocytes in the solution. By this means, a part of proteins contained in human chondrocytes can be decomposed with a protease. In fact, it is preferred that proteases such as collagenases be allowed to act on human chondrocytes without completely decomposing human chondrocytes. Because of this, it is preferred that 0.01 wt % or more and 1 wt % or less (or 0.1 wt % or more and 0.5 wt % or less) of protease be contained in a solution. The immersion time is preferably adjusted to, for example, 3 to 24 hours.

The inhibitor-treatment step is a step for treating a tissue with an inhibitor of a protease after the enzymatic treatment step. The step is a step for bringing a tissue treated with a protease into contact with an inhibitor of the protease to inhibit the function of the protease. An example of inhibitors is a trypsin inhibitor or a collagenase inhibitor. An example of the trypsin inhibitor and the collagenase inhibitor is a soybean-derived protease inhibitor. Other examples of the collagenase inhibitor are retinol acid disclosed in JP 5044071 B2, and an 8-hydroxyquinoline derivative disclosed in JP H5-97674 A. Retinol acid can be prepared in the form of salt or solvate. The salt and solvate are as described below. This inhibitor-treatment step can be also carried out in the same manner as in the above enzymatic treatment step. The inhibitor-treatment step is, for example, only necessary to prepare a solution containing an inhibitor of a protease and to immerse human chondrocytes in the solution. By this means, the function of a protease contained in human chondrocytes can be inhibited. As described above, the present invention can effectively culture good chondrocytes by including the inhibitor-treatment step.

That is, collagen is expressed by culturing chondrocytes. Because of this, normally it is not thought that the collected chondrocytes are treated with a collagenase. The chondrocytes are surrounded by an extracellular matrix of, for example, collagen in a cartilage tissue. In the present invention, therefore, in order to take out chondrocytes from the matrix, the collected chondrocytes are purposely treated with a collagenase and trypsin to decompose components which are not suitable for culture of chondrocytes and post-transplantation. However, when trypsin continues to show the function, chondrocytes are damaged, and the culture of chondrocytes does not proceed. In the present invention, therefore, the function of a protease such as trypsin is inhibited in the inhibitor-treatment step. Because a protease inhibitor-like component exists in a serum, a protease inhibitor is not required to be added to a culture medium using a serum. Conversely, a serum-free culture medium does not have an enzyme inhibitor-like component, and thus an enzyme inhibitor-like component is added to inhibit the function of a protease. Also, in a case in which a collagenase is used, a collagenase inhibitor can be used. However, because the act of a collagenase is not strong, a collagenase inhibitor does not have to be used.

The culture step is a step for culturing a tissue in a serum-free culture medium after the inhibitor-treatment step. The serum-free culture of chondrocytes has been already known as mentioned above. Therefore, a known culture method can be appropriately applied also in the present invention. In the present invention, it is preferred that a serum-free culture medium contain a smoothened agonist. A smoothened or smoothened receptor is a protein to activate Sonic hedgehog (Shh) as described in, for example, JP 5270362 B2 and JP 5424923 B2. The smoothened agonist is preferably SAG or SAG1.1. SAG is a compound known as CAS No. 364590-63-6, the chemical substance name of which is N-methyl-N'-(3-pyridinylbenzyl)-N'-(3-chlorobenzo[b]thiophene-2-carbonyl)-1,4-diaminocyclohexane. SAG is a protein to activate Sonic hedgehog (Shh) as disclosed in WO 2014/084085 A. SAG1.1 has a chemical substance name of N-methyl-N'-(3-(4-benzonitrile)-4-methoxybenzyl)-N-(3-chlorobenzo[b]thiophene-2-carbonyl)-1,4-diaminocyclohexane. SAG is described in detail in Documents, Sinha S, Chen J K. Nat Chem Biol. 2006 January; 2(1): 29-30 and Chen J K, Taipale J, Young K E, Maiti T, Beachy P A. Proc Natl Acad Sci USA. 2002 Oct. 29; 99(22): 14071-6. Similarly, SAG1.1 is described in detail in a Document, Chen, W., Ren, X. R., Nelson, C. D., Barak, L. S., Chen, J. K., Beachy, P. A., de Sauvage, F. & Lefkowitz, R. J. (2004) Science 306, (5705) 2257-2260.

The method for culturing chondrocytes can be carried out appropriately based on common experiences and knowledge. As a serum-free culture medium, one obtained by appropriately adding reagents to a base medium can be used. As the amount of reagents, a known amount can be appropriately modified and used.

The present invention also provides a serum-free culture medium. This serum-free culture medium preferably contains a smoothened agonist (e.g. SAG). This culture medium is preferably used to culture chondrocytes. Because of this, this serum-free culture medium is a serum-free culture medium containing chondrocytes during culture.

The culture medium of the present invention preferably contains kartogenin. Kartogenin, the substance name of which is 2-[(biphenyl-4-yl)carbamoyl] benzoic acid, is on the market. It is preferred that the culture medium of the present invention contain either of kartogenin and SAG, or both, and the culture medium can be one which contains only kartogenin, one which contains only SAG, or one which contains both kartogenin and SAG.

The serum-free culture medium of the present invention can be obtained by appropriately adding necessary elements to a base medium. Examples of the base medium are Eagle's Basal Medium and DMEM. As reagents, known ones which are used for culture media can be appropriately added. Examples of the reagents are the above-mentioned SAG (or SAG1.1), FGF2 (beads), IGF (insulin-like growth factor), insulin, steroids such as HC (hydrocortisone), PDGF (platelet derived growth factor), ACTH (adrenocorticotropic hormone), LIF (leukemia inhibitory factor), TGFβ, BMP, steroids, fatty acids, soybean trypsin inhibitors, ascorbic acid, hyaluronic acid, proline, dexamethasone, transferrin, and selenous acid. In case, ascorbic acid is added to a culture medium, one in the form of salt such as 2-phosphate can be added.

In JP 5228187 B2, for example, a medium composition for culturing chondrocytes, characterized by containing glucuronic acid, is disclosed. Also in the present invention, for example, additives of a culture medium described in this publication can be appropriately used.

Insulin is preferably one which is added as ITS. ITS is a reagent containing insulin, transferrin and sodium selenite, and its composition example is 5 μg/ml insulin, 5 μg/ml transferrin and 5 ng/ml sodium selenite. Because ITS is on the market, one on the market can be appropriately used. ITS is preferably an animal-free one which does not contain components derived from animals. In the present invention, raw materials which do not basically contain components derived from animals are preferably used.

SAG, kartogenin, FGF2, IGF (insulin-like growth factor), insulin, steroids such as hydrocortisone, PDGF, ACTH (adrenocorticotropic hormone), LIF (leukemia inhibitory factor), TGFβ, BMP, steroids, and ITS can be each added to a culture medium so that the concentration is, for example, 0.1 ng/mL or more and 20 μg/mL or less (or 0.2 ng/mL or more and 10 μg/mL or less). These can be appropriately adjusted depending on the degree of purification and the amount required, and added. As a result of trial and error, it was found that the serum-free culture medium was preferably one which uses as a base a culture medium in which SAG (e.g. 0.05 to 5 μM, preferably 0.1 μM to 2 μM, preferably 0.2 μM to 1 μM), FGF2 (e.g. 1 ng/mL to 1 μg/mL), IGF (e.g. 1 ng/mL to 50 μg/mL), and HC (e.g. 1 ng/ML to 1 μg/mL) are added to a base medium.

The above-mentioned cells are cultured and proliferated in the common culture conditions (e.g. 37° C., 5% $CO_2$). As the amount, cells can be in a state from about 10% to 100% confluent, and culture can be also done in a high density and multilayered state, for example, over 100% confluent. Immediately after or after a while from a transplant, the state can be transferred to a hypoxic state. Hypoxic culture can be done using a hypoxic incubator of a type that the partial pressure of oxygen is reduced, for example, by mixing for example commercially available nitrogen gas, or can be done, for example, by blowing, for example, nitrogen gas into a suitable space to reduce the partial pressure of oxygen.

The culture step carried out in examples is as described below. That is, the above-mentioned SAG was added to a culture medium. Ascorbic acid and fatty acids are appropriately added to the culture medium. As a result of repeated experiments, in a case in which ascorbic acid and fatty acids were contained from the onset of culture, chondrocytes were not successfully proliferated. On the other hand, in a case in which ascorbic acid and fatty acids were added after a predetermined period from the onset of culture, chondrocytes obviously increased. Therefore, ascorbic acid, an ascorbic acid salt or an ascorbic acid solvate is preferably added to a serum-free culture medium during a period from the 3rd day to 28th day after the onset of culture. The time to add ascorbic acid can be during a period from the 5th day to 25th day after the onset of culture, during a period from the 10th day to 22nd day, or during a period from the 14th day to 21st day, and can be also during a period by appropriately shortening or extending these periods. In addition, a fatty acid, a fatty acid salt or a fatty acid solvate is preferably added to a serum-free culture medium during a period from the 3rd day to 28th day after the onset of culture. The time to add a fatty acid and the like can be from a period from the 5th day to 2nd month after the onset of culture, from a period from the 10th day to 40th day, or from a period from the 19th day to 25th day. By doing such culture, chondrocytes could be significantly effectively cultured compared to those of control.

The chondrocytes or cartilage produced in the method of the present invention can be used for a cartilage transplant which is carried out as a surgical technique to repair cartilage, for example, in arthritis disorders (e.g. non-metabolic bone diseases such as bone fractures in the field of orthopedics, refractures, bone deformity and spondylosis deformans, osteosarcomas, myelomas, osteogenesis imperfecta and scoliosis; metabolic bone diseases such as bone defects, osteoporosis, osteomalacia, rickets, osteitis fibrosa, renal osteodystrophy, Paget's disease of bone and ankylosing spondylitis; and chondropathy such as arthritis deformans, and chronic rheumatoid arthritis). The method for transplanting cartilage can be carried out using a usual unit. Therefore, chondrocytes or cartilage produced in the method of the present invention can be used as a safe and low toxic preventive and therapeutic agent to the above-mentioned arthritis disorders. In addition, using the present culture system, genes related to cartilage differentiation can be searched, and pharmaceutical products can be also searched.

Collection of Cultured Cells

Chondrocytes cultured as mentioned above form aggregates which are created by accumulation of cells. Therefore, for example, when a bar is inserted into a culture medium from the lateral direction after culture and pulled up, a culture of a cartilage tissue can be effectively collected. Normally, it is required that the cartilage tissue be peeled off from a container to collect cultured cells. In a common method, a protease such as a collagenase or trypsin has been allowed to act to peel off chondrocytes from a container. Cartilage tissues obtained by culture have been scattered. In the culture method of the present invention, aggregates created by accumulation of chondrocytes are easily peeled off, and thus only using the above-mentioned collecting method, a cartilage tissue for example in the form of sheet or mass can be easily collected.

Example 1

Digestion of Tissue—Preparation of Culture—

Primary human chondrocytes were isolated from a fresh sample of articular cartilage, and the sample was fractionated. The obtained fractionated sample was then immersed in a 0.1% to 0.3% collagenase solution, and subjected to enzymatic digestion at 37° C. for 4 to 5 hours. The obtained cells were collected by centrifugation for 5 minutes at 1,200 rpm.

A mixture obtained by adding 100 ng/mL FGF, 0.5 µM SAG, 400 ng/mL HC, 5 ng/mL IGF, and 5 µg/mL insulin to DMEM medium was used as a culture medium. The cultured cells previously obtained were seeded at a density of 1000 cells/cm$^2$ and cultured in an environment of 37° C. and 5% $CO_2$.

FIG. 1 is a photograph substituted for drawings showing the cultured chondrocytes from the 0th day to 16th day of culture in Example 1. The figure shows that cartilage tissues gradually increased.

Figure 2:
FIG. 2 is a photograph substituted for drawings showing the cultured chondrocytes from the 19th day to 41st day of culture in Example 1.
Figure 2:
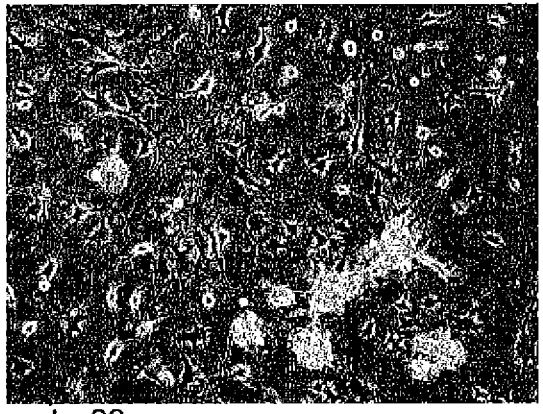
Figure 2:
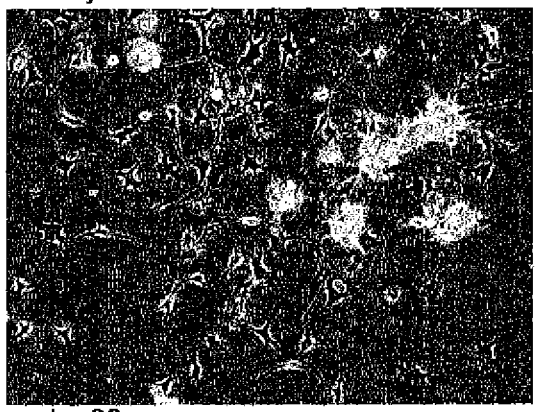
Figure 2:
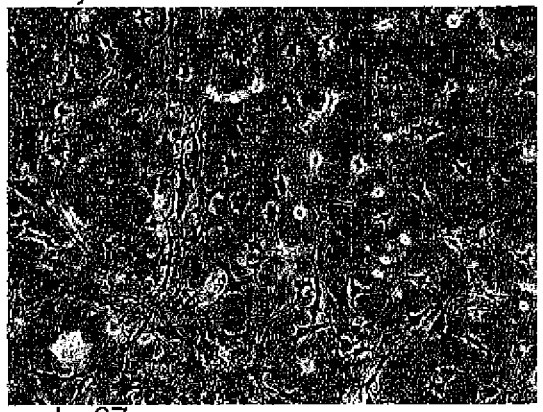
Figure 2:
Figure 2:
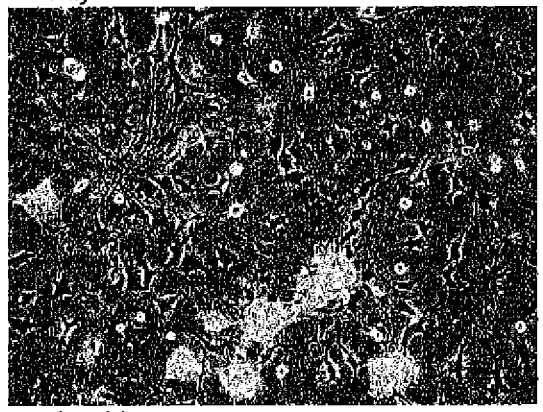

FIG. 2 is a photograph substituted for drawings showing the cultured chondrocytes from the 19th day to 41st day of culture in Example 1. On the 18th day of culture, 50 µg/mL ascorbic acid was added to the culture medium. As a result of trial and error, it was found that the addition of ascorbic acid in that long of period was very effective for culture of chondrocytes in a serum-free culture medium. On the 3rd week day of culture, fatty acids were added at from 1:1000 to 1:500. When fatty acids were added, the number of cells increased and the viscosity of the culture medium increased.

Fatty acids and cholesterol added during culture are as follows.

| Fatty acids and Cholesterol Added during Culture | |
|---|---|
| | Concentration mg/mL |
| Arachidonic acid | 2.0 |
| Linoleic acid | 10.0 |
| Linolenic acid | 10.0 |
| Myristic acid | 10.0 |
| Oleic acid | 10.0 |
| Palmitic acid | 10.0 |
| Palmitoleic acid | 10.0 |
| Stearic acid | 10.0 |
| Cholesterol | 220.0 |
| DL-α-tocopherol acetate (vitamin E) | 70.0 |

The above-mentioned amount added can increase or decrease within a range of ±200% and preferably ±100%. The range of fatty acids can be a range of 1:50 to 1:2000.

In the case of subculture, trypsin was used in place of a collagenase, and the collected cells were immersed in a soybean-derived protease inhibitor, a trypsin inhibitor.

Comparative Example 1

Figure 3:
FIG. 3 is a photograph substituted for drawings showing the cultured chondrocytes from the first day to 5th day of culture in Comparative Example 1.
Figure 3:
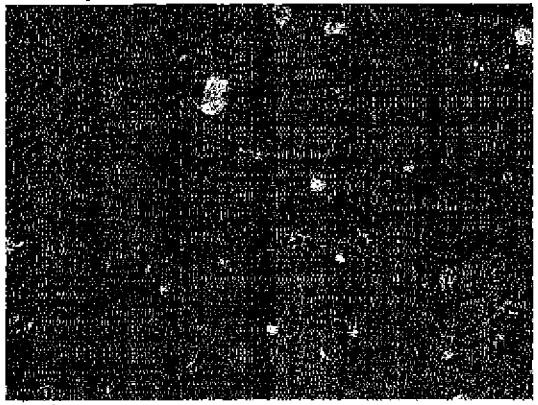

FIG. 3 is a photograph substituted for drawings showing the cultured chondrocytes from the first day to 5th day of culture in Comparative Example 1. In this example, cartilage was cultured in the same manner as in Example 1 except that DMEM medium not containing SAG was used. As shown in FIG. 3, it was shown that chondrocytes could not be effectively cultured in the state without SAG.

Adjustment of Time to Add Ascorbic Acid and Fatty Acids

The addition of ascorbic acid was begun at the onset of culture, and after an hour, 3 hours, 12 hours, a day, two days, 3 days, 5 days, a week, 10 days, 2 weeks, 20 days, 3 weeks, 25 days, 4 weeks, 30 days, 5 weeks, 40 days, 6 weeks, 45 days, 7 weeks, 50 days, 8 weeks, 60 days, 9 weeks, and 70 days from the onset of culture. Ascorbic acid was added at regular intervals (e.g. every 12 hours, every day, every two days).

The addition of fatty acids was adjusted in the same manner as in the addition of ascorbic acid.

As a result, it was found that the addition of ascorbic acid after about 3 days from the onset of culture was more desired than the addition of ascorbic acid immediately after the onset thereof.

The addition of fatty acids was similar to the addition of ascorbic acid, and it was found that the addition of fatty acids after the addition of ascorbic acid was more desired.

Example 2

A mixture obtained by adding 100 ng/mL FGF2, 0.5 µM SAG, 400 ng/mL HC, 5 ng/mL IGF and 5 µg/mL insulin to DMEM medium was used as a culture medium for subculture. The cultured cells in Example 1 were seeded at a density of 10000 cells/cm$^2$ and cultured in an environment of 37° C. and 5% $CO_2$.

Figure 4:
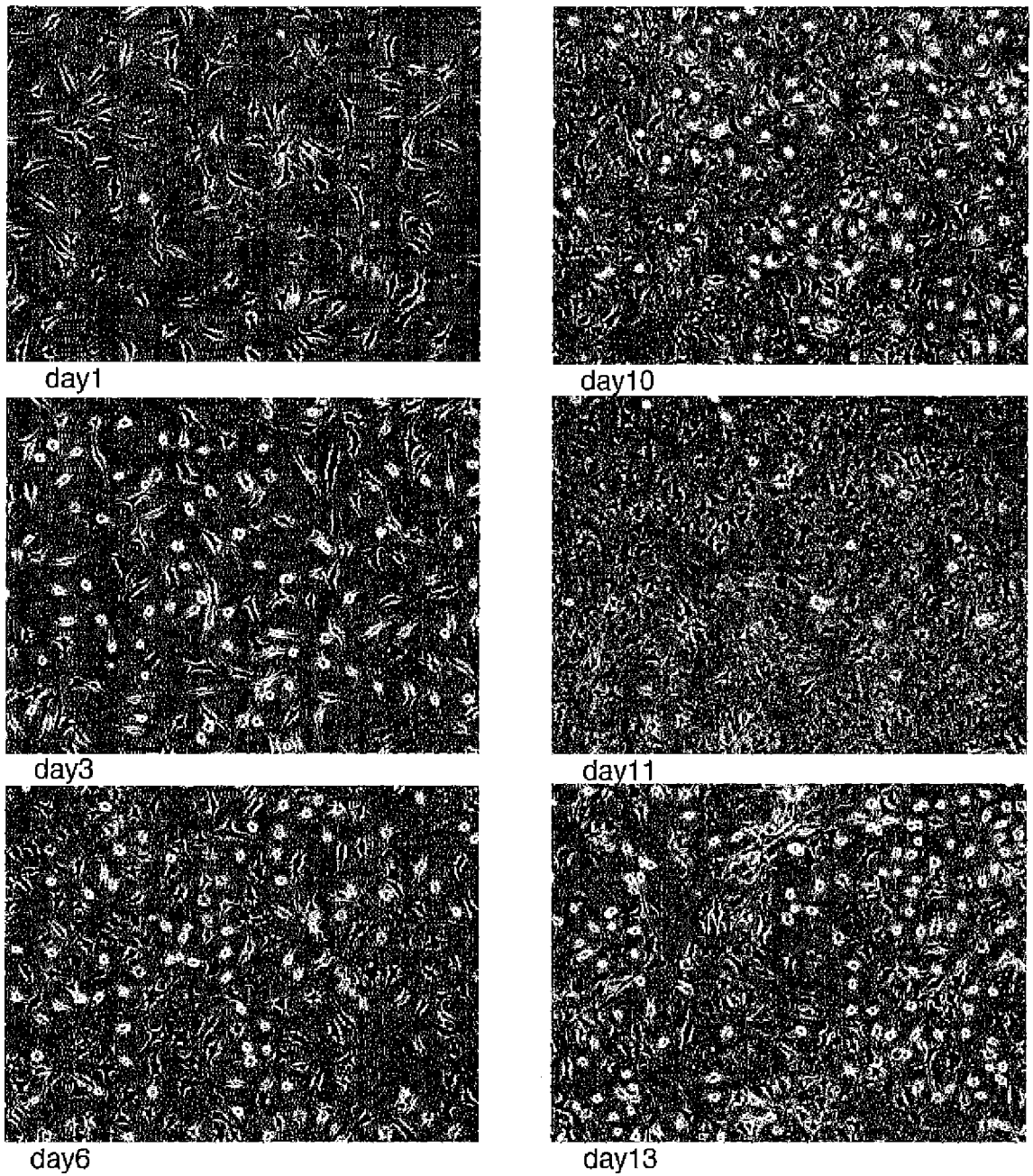
FIG. 4 is a photograph substituted for drawings showing the cultured chondrocytes from the first day to 13th day of culture in Example 2 (subculture).

FIG. 4 is a photograph substituted for drawings showing the cultured chondrocytes from the first day to 13th day of culture in Example 2 (subculture). It was observed that after about 10 days from the onset of culture, viscosity was developed in the culture medium and, when removing the culture medium with an aspirator, slim threads were generated. The viscosity of the culture medium had increased from the 13th day.

Figure 5:
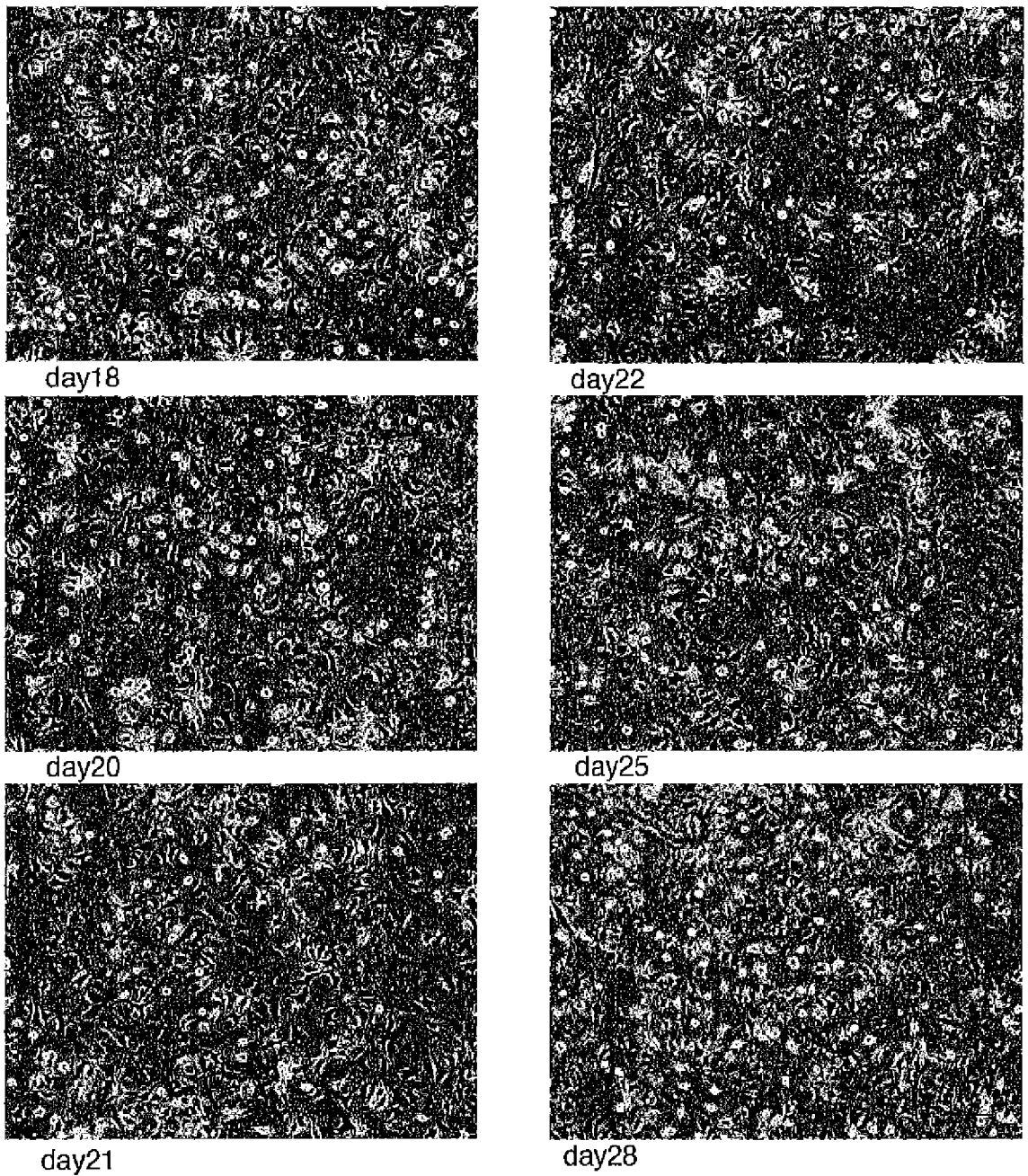
FIG. 5 is a photograph substituted for drawings showing the cultured chondrocytes from the 18th day to 28th day of culture in Example 2.

FIG. 5 is a photograph substituted for drawings showing the cultured chondrocytes from the 18th day to 28th day of culture in Example 2. On the 18th day of culture, 50 µg/mL ascorbic acid was added to a culture medium. As a result of trial and error, it was found that the addition of ascorbic acid in that long of period was very effective for culture of chondrocytes in a serum-free culture medium. On the 3rd week day of culture, fatty acids were added at 1:1000 to 1:500. When fatty acids were added, the number of cells increased and the viscosity of the culture medium increased.

Figure 6:
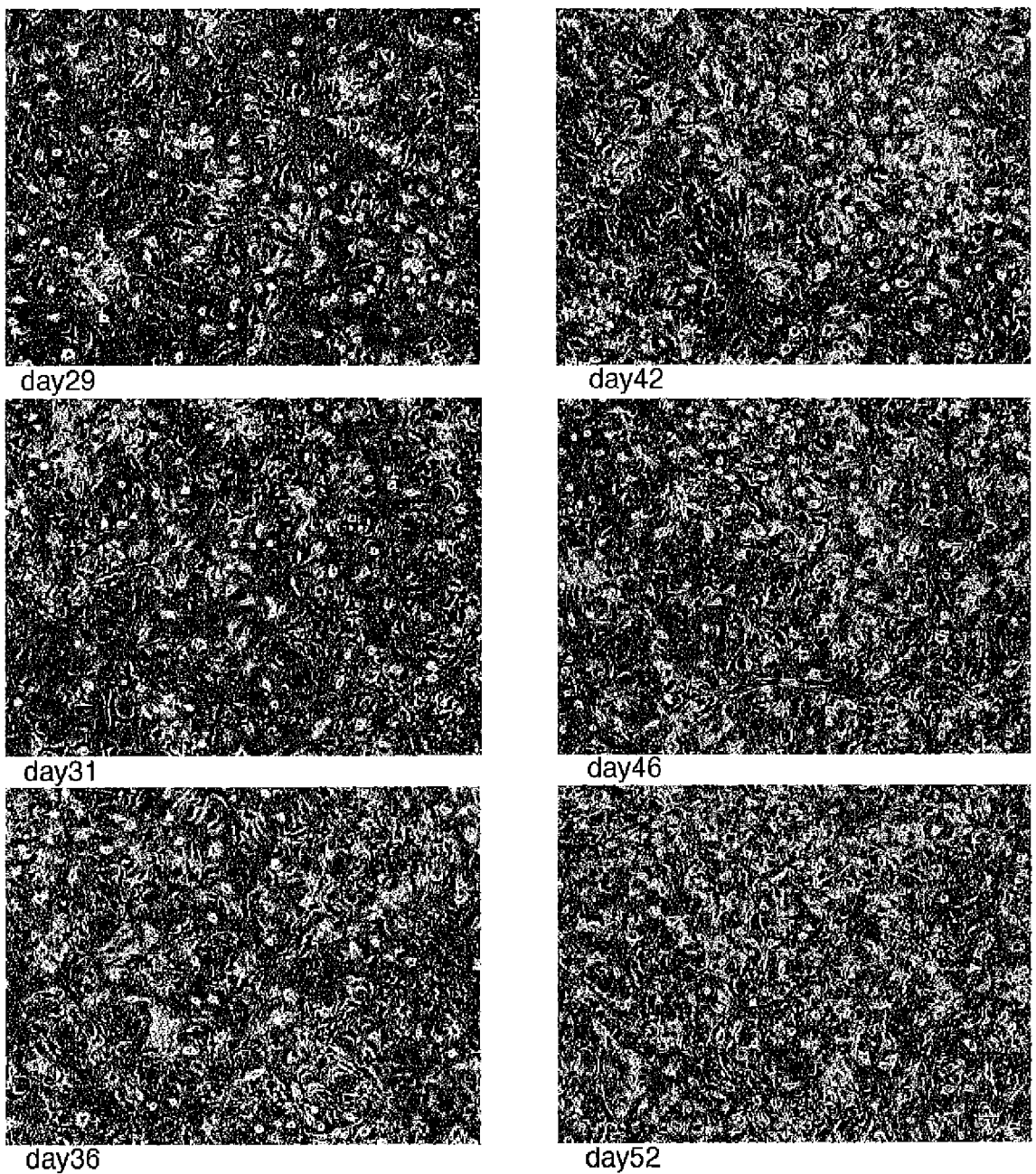
FIG. 6 is a photograph substituted for drawings showing the cultured chondrocytes from the 29th day to 52nd day of culture.

FIG. 6 is a photograph substituted for drawings showing the cultured chondrocytes from the 29th day to 52nd day of culture. When removing the culture medium with an aspirator, thick threads were generated. As shown in figures, it was shown that chondrocytes could be effectively cultured by culturing chondrocytes using a serum-free culture medium.

Fatty acids and cholesterol added during culture are as follows.

| Fatty acids and Cholesterol Added during Culture | |
|---|---|
| | Concentration mg/ML |
| Arachidonic acid | 2.0 |
| Linoleic acid | 10.0 |
| Linolenic acid | 10.0 |
| Myristic acid | 10.0 |
| Oleic acid | 10.0 |
| Palmitic acid | 10.0 |
| Palmitoleic acid | 10.0 |
| Stearic acid | 10.0 |
| Cholesterol | 220.0 |
| DL-α-tocopherol acetate (vitamin E) | 70.0 |

The above-mentioned amount added can increase or decrease within a range of ±200% and preferably ±100%. The range of fatty acids can be a range of 1:50 to 1:2000.

Comparative Example 2

Figure 7:
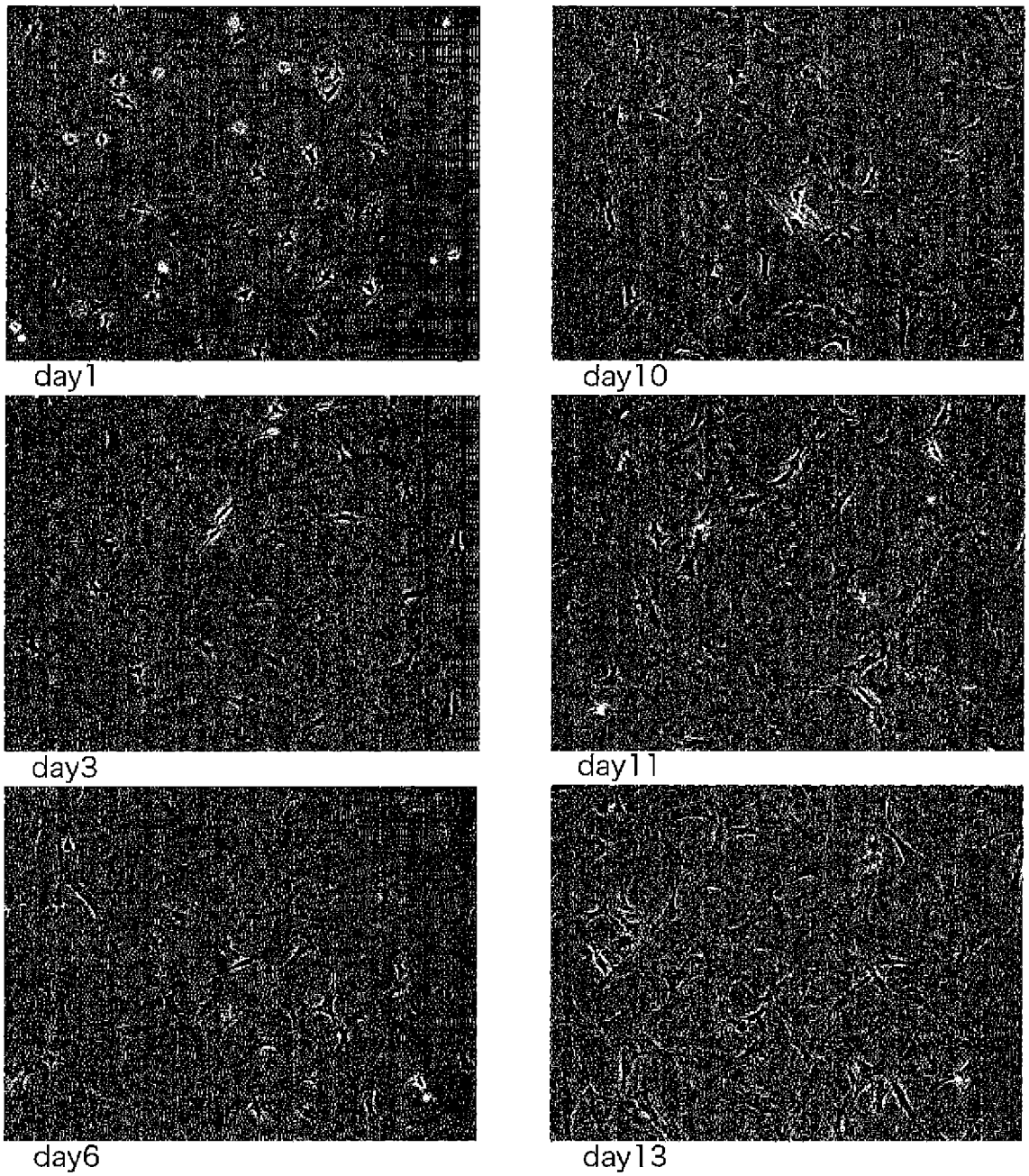
FIG. 7 is a photograph substituted for drawings showing the cultured chondrocytes from the first day to 13th day of culture in Comparative Example 2. In this example, cartilage was cultured in the same manner as in Example 2 except that DMEM medium not containing SAG was used.

FIG. 7 is a photograph substituted for drawings showing the cultured chondrocytes from the first day to 13th day of culture in Comparative Example 2. In this example, cartilage was cultured in the same manner as in Example 2 except that DMEM medium not containing SAG was used. As shown in FIG. 7, it was shown that chondrocytes could not be effectively cultured in the state which does not contain SAG.

Example 3

In order to verify whether chondrocytes cultured in the serum-free culture medium of the present invention are cells suitable for a transplant, the cells were transplanted to a nude mouse, and it was examined whether cartilage was formed in vivo.

First, chondrocytes derived from human auricular cartilage were prepared in accordance with a procedure described in Example 1, and cultured in the serum-free culture medium of the present invention. The chondrocytes after culture were immersed in collagen cotton, and then transplanted to two portions of the dorsum of a nude mouse with the cotton. The transplant operation and the control of nude mice were carried out in accordance with a known method. After 6 months from the transplant, the dorsum of the nude mouse was incised, and it was verified whether or not cells were fixed to the transplant site and cartilage was formed.

Figure 8:
FIG. 8 is a photograph substituted for a drawing showing a state in which human auricular cartilage cultured in a serum-free culture medium was transplanted into the dorsum of a nude mouse, and cartilage was formed after 6 months.

FIG. 8 is a photograph showing a state in which the dorsum of a nude mouse was incised after 6 months from the transplant. Large white cartilages (A-2, B-2) were verified in the sites to which the cultured chondrocytes were transplanted (the left and right sides of the dorsum). Therefore, it was thought that the cultured cells had been fixed on the transplant sites and proliferated to form cartilage.

Figure 9:
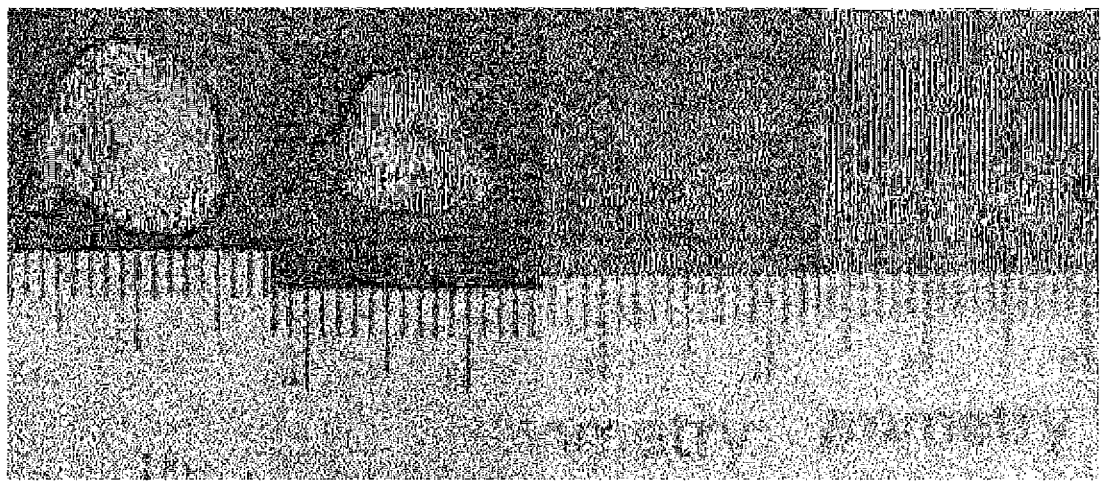
FIG. 9 is a photograph substituted for a drawing showing specimens obtained by taking out cartilages formed in the dorsum of nude mice.
Figure 10:
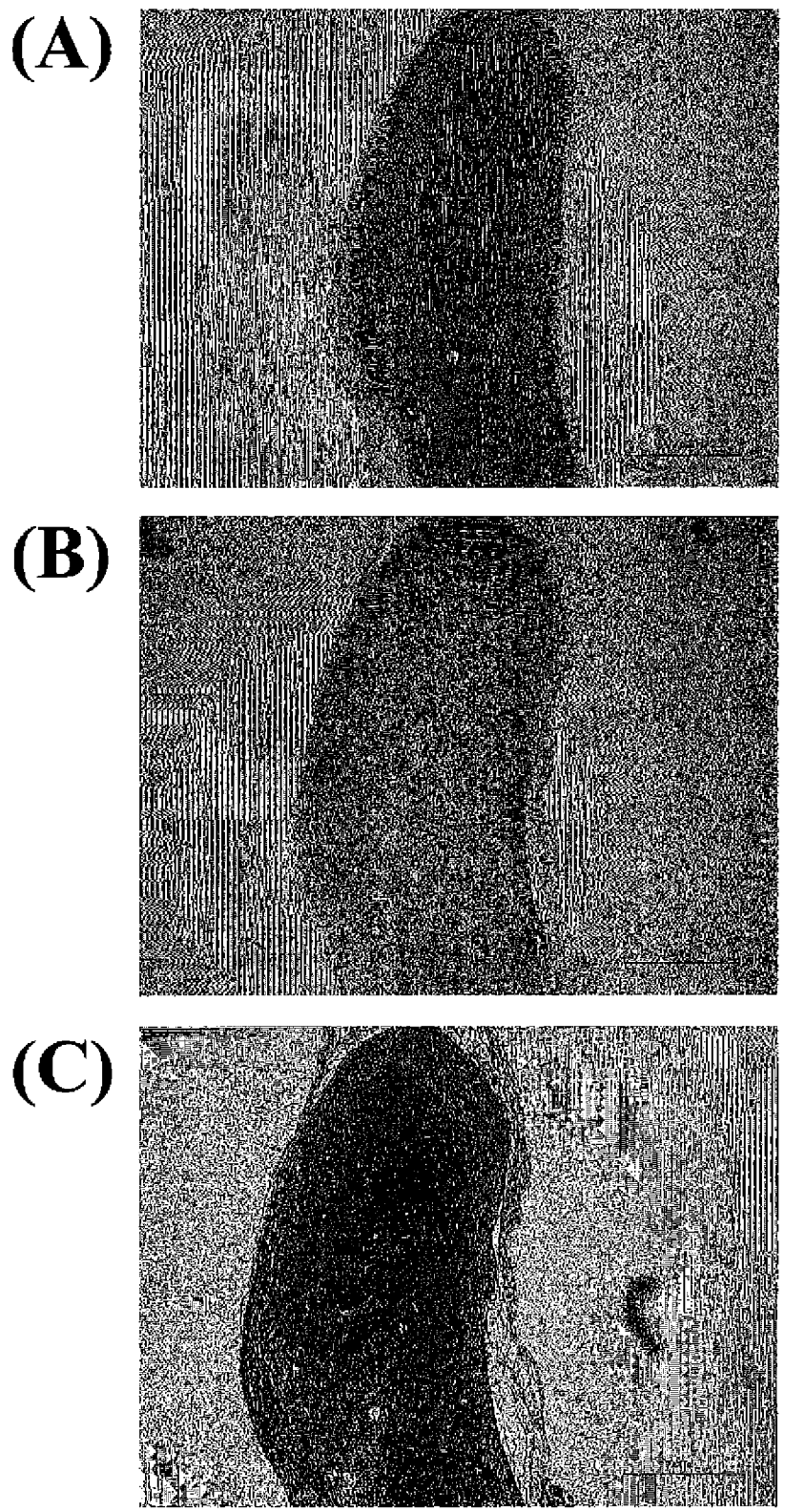
FIGS. 10(A) to 10(C) are photographs substituted for drawings showing the results in which sections of cartilage formed by transplanting human auricular cartilage cultured in a serum-free culture medium (SAG+ITS) into the dorsum of a nude mouse were stained with toluidine blue, alcian blue or EVG (Elastica Vangeson).
Figure 11:
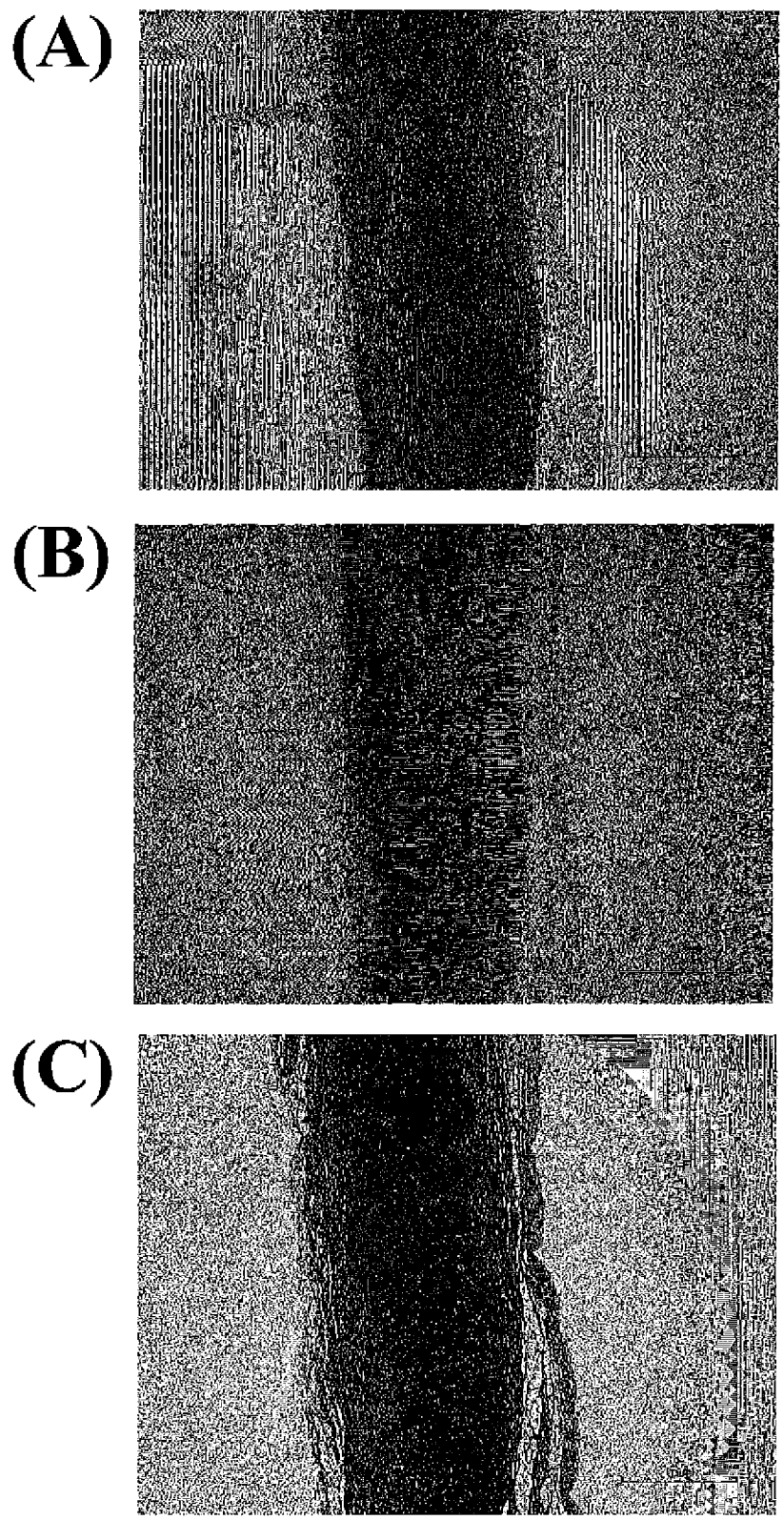
FIGS. 11(A) to 11(C) are photographs substituted for drawings showing the results in which sections of cartilage formed by transplanting human auricular cartilage cultured in a serum-free culture medium (Kartogenin+ITS) into the dorsum of a nude mouse were stained with toluidine blue, alcian blue or EVG.

FIG. 9 shows a state in which the cartilage formed in the dorsum of a nude mouse was extracted. A1 shows cartilage formed in a nude mouse to which chondrocytes cultured in the following culture condition (A) (SAG+ITS) were transplanted. As ITS, an animal-free one was used.

Culture Condition (A)
DME (H):F-12=1:1
SAG 0.1 uM
FGF 50 ng/mL
HC 400 ng/mL
ITS ×1
From the 8th day of culture, 50 ug/mL ascorbic acid and 1:500 of fatty acid were added.

C1 shows cartilage formed in a nude mouse to which chondrocytes, which were cultured in the following culture condition (C) (Kartogenin+ITG) and had a tendency to separate from a culture medium and had the lowest viscosity, were transplanted.

Culture Condition (C)
DME (H):F-12=1:1
Kartogenin 1 uM
FGF 50 ng/mL
HC 400 ng/mL
ITS ×1
From the 8th day of culture, 50 ug/mL ascorbic acid and 1:500 of fatty acid were added.

The chondrocytes cultured in the culture condition (A) formed larger cartilage than the chondrocytes cultured in the culture condition (C). In addition, in a nude mouse to which only the collagen cotton was transplanted (negative control), cartilage was not formed (D2 and D3).

Next, it was histologically examined that cartilage formed in the site to which cultured cells were transplanted was cartilage. Specifically, sections of the extracted cartilages (A1, C1) were produced, and stained using toluidine blue and alcian blue which specifically strain cartilage. In addition, cartilage was stained using EVG (Elastica Vangeson) which specifically stains elastic cartilage. The results were shown in FIG. 10(A) to FIG. 11(C).

FIGS. 10(A) to 10(C) show the stain results of A1 cartilage. FIG. 10(A) is the result of toluidine blue stain, and cartilage was stained into purple. FIG. 10(B) is the result of alcian blue stain, and cartilage was stained into blue. Therefore, it was verified that A1 cartilage was positive for both stains and had the properties of cartilage.

In addition, FIG. 10(C) shows the result of EVG stain, and cartilage was stained into brown. Therefore, the cartilage was proved to be elastic cartilage, and identified to be auricular cartilage.

FIGS. 11(A) to 11(C) show the stain results of C1 cartilage. FIG. 11(A) is the result of toluidine blue stain, and cartilage was stained into purple. FIG. 11(B) is the result of alcian blue stain, and cartilage was stained into blue. Therefore, it was verified that C1 cartilage was positive for both stains and had the properties of cartilage.

In addition, FIG. 11(C) shows the result of EVG stain, and cartilage was stained into brown. Therefore, the cartilage was proved to be elastic cartilage, and identified to be auricular cartilage.

Therefore, it was proved that chondrocytes cultured in the serum-free culture medium of the present invention were cells suitable for a transplant, and when the cells were transplanted to a nude mouse, cartilage could be formed in the transplant site.

Example 4

Figure 12:
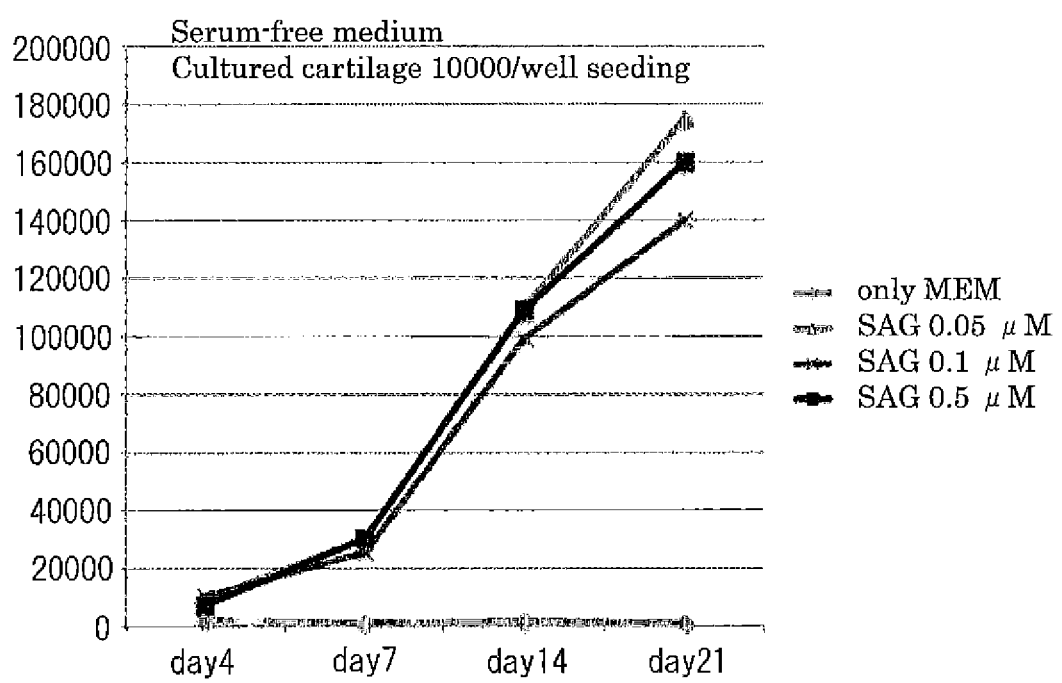
FIG. 12 is a graph showing the relationship between the SAG concentration and the proliferation of the cultured chondrocytes.

In order to examine the optimum concentration of SAG added to a culture medium, the concentration of SAG in a serum-free culture medium was changed to 0.05 uM, 0.01 uM or 0.5 uM, and an influence on proliferation of cultured chondrocytes was examined. Specifically, chondrocytes prepared in the same procedure as in Example 1 were seeded at a density of 10000 cells/well, and the number of cells on the 4th, 7th, 14th and 21st day after seeding was measured. The results were shown in FIG. 12.

In all the SAG concentrations, a difference in cell proliferation up to the 14th day of culture was not hardly observed, and an obvious difference which had been expected was not observed also on the 21st day of culture.

Figure 13:
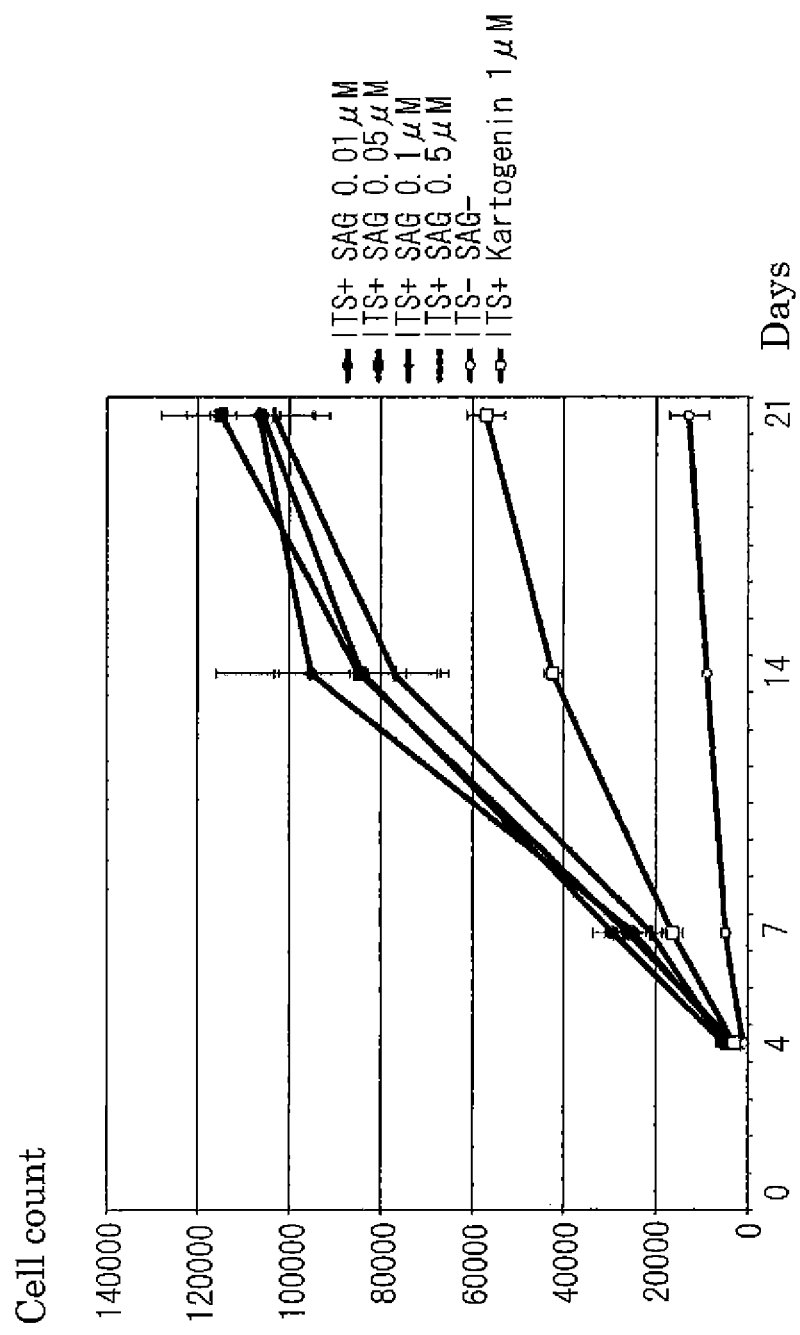
FIG. 13 is a graph showing the relationship between the SAG concentration and the proliferation of the cultured chondrocytes in a case in which ITS and SAG are added to a culture medium.

Because SAG is a very expensive reagent, it is preferred that SAG be able to be used at as low concentration as possible. This was verified because the inventors obtained knowledge that a low concentration of SAG can sufficiently promote the proliferation of chondrocytes by adding ITS (Insulin-Transferrin-Selenium) along with SAG. Specifically, the concentration of SAG in a serum-free culture medium to which ITS had been added was changed to 0.01 uM, 0.05 uM, 0.1 uM or 0.5 uM, and the cultured chondrocytes were cultured, and the number of cells on the 4th, 7th, 14th and 21st day after seeding was measured. The results were shown in FIG. 13.

In a case in which both ITS and SAG were not added, a remarkable effect on proliferation of chondrocytes was not observed. On the other hand, in a case in which SAG was added along with ITS, an increase in chondrocytes was almost equally observed at any of the SAG concentration from 0.01 uM to 0.5 uM. Therefore, it was revealed that when SAG was added along with ITS, a sufficient effect could be obtained even at a SAG concentration of 0.01 uM.

It was also revealed that the addition of kartogenin in place of SAG was also effective for the proliferation of chondrocytes.

Figure 14:
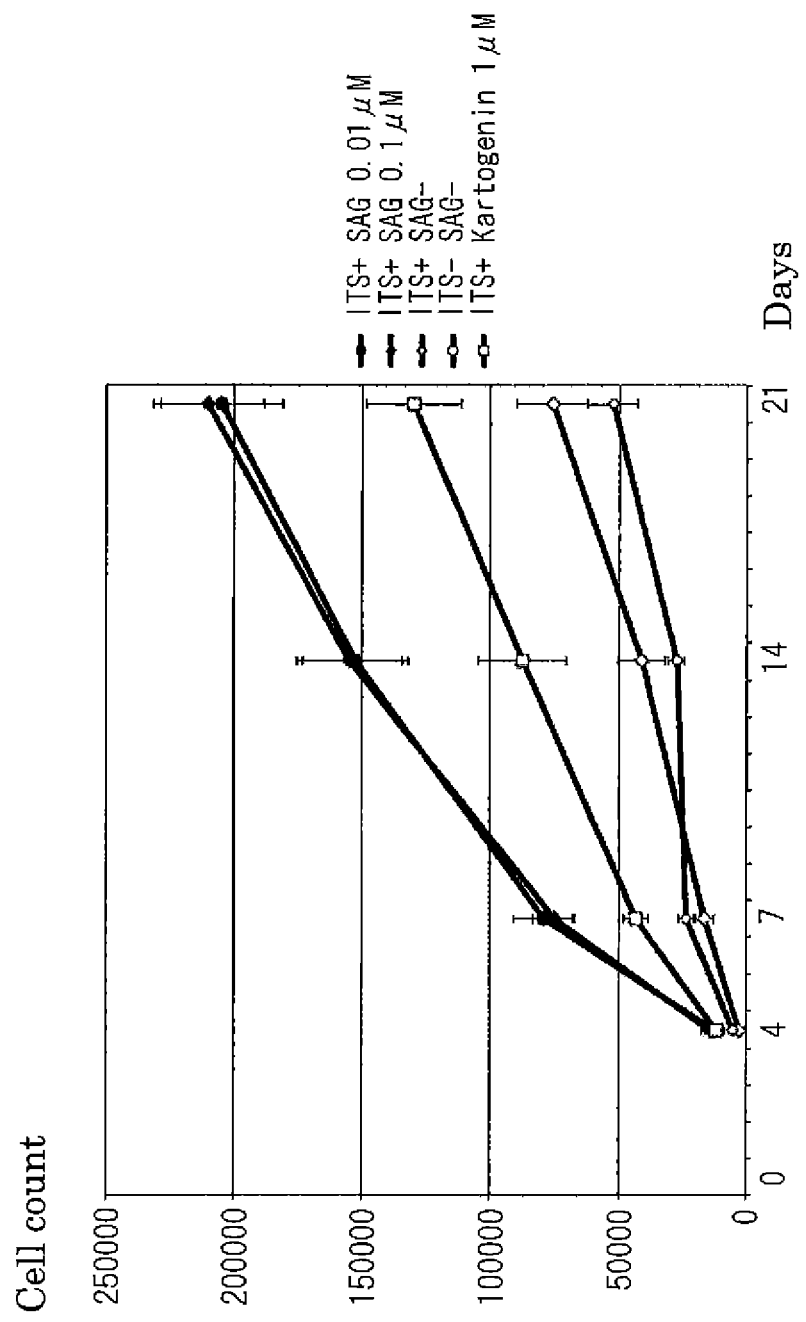
FIG. 14 is another graph showing the relationship between the SAG concentration and the proliferation of the cultured chondrocytes in a case in which ITS and SAG are added to a culture medium.

In order to further examine the effect of ITS and SAG on an increase in chondrocytes, an increase in chondrocytes was examined in treated sites to which both ITS and SAG were added (ITS+ 0.01 uM SAG, ITS+ 0.1 uM SAG), a treated site to which ITS was added alone (ITS+ SAG−), and a treated site to which ITS and SAG were not added (ITS− SAG−). The results were shown in FIG. 14.

The effect on proliferation of chondrocytes was the lowest in the treated site to which ITS and SAG were not added (ITS− SAG−). In the treated site to which ITS was added alone (ITS+ SAG−), the proliferation effect was slightly observed. However, the effect was lower than that of the treated sites to which both ITS and SAG were added. Therefore, it can be said that the effect of ITS on proliferation of chondrocytes is not very strong, and an obvious effect can be obtained by combining SAG.

It was also found that in a treated site in which ITS and kartogenin were combined (ITS+ 1 uM Kartogenin), the effect on proliferation of chondrocytes was observed. However, the effect was lower than that of the case in which ITG and SAG were combined.

These results verified that the addition of SAG along with ITS was effective for the proliferation of chondrocytes. It was also verified that the addition of kartogenin along with ITS was also effective.

INDUSTRIAL APPLICABILITY

The serum-free culture medium and the method for culturing chondrocytes of the present invention can be used to produce cultured cartilage. Because of this, they can be used in the field of the present invention and pharmaceutical industry.

The invention claimed is:

1. A serum-free culture medium for culturing human chondrocytes, comprising:
   human auricular cartilage, ITS (a reagent containing insulin, transferrin and sodium selenite), FGF2 (fibroblast growth factor 2) and hydrocortisone, and further comprising SAG (a smoothened agonist) at a concentration of at least 0.01 µM.

2. The culture medium according to claim 1, further comprising kartogenin.

3. The culture medium according to claim 1, further comprising IGF (insulin-like growth factor).

4. The culture medium according to claim 1, further comprising chondrocytes, which are cultured.

5. A culture medium kit, comprising the culture medium according to claim 1, and an ascorbic acid agent and a fatty acid agent,
   wherein the ascorbic acid agent includes ascorbic acid, an ascorbic acid salt or an ascorbic acid solvate, and
   the fatty acid agent includes a fatty acid, a fatty acid salt or a fatty acid solvate.

* * * * *